United States Patent
Anderson et al.

(10) Patent No.: US 6,285,816 B1
(45) Date of Patent: Sep. 4, 2001

(54) WAVEGUIDE

(75) Inventors: Marc A. Anderson, Madison, WI (US); Lawrence W. Miller, New York, NY (US); Maria Isabel Tejedor-Anderson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/291,261

(22) Filed: Apr. 13, 1999

(51) Int. Cl.[7] .................................................... G02B 6/00
(52) U.S. Cl. ........................ 385/141; 385/128; 385/129; 385/130; 385/144
(58) Field of Search ..................................... 385/123, 125, 385/126–130, 141, 142, 144

(56) References Cited

U.S. PATENT DOCUMENTS

| | | | |
|---|---|---|---|
| 3,801,352 | * 4/1974 | Furuuchi et al. | 117/62 |
| 4,597,913 | * 7/1986 | Kimoto et al. | 558/436 |
| 4,604,248 | * 8/1986 | Dehm | 264/3.1 |
| 4,987,158 | * 1/1991 | Eckberg | 77/6 |
| 4,997,576 | 3/1991 | Heller et al. | |
| 5,028,568 | 7/1991 | Anderson et al. | |
| 5,035,784 | 7/1991 | Anderson et al. | |
| 5,096,745 | 3/1992 | Anderson et al. | |
| 5,104,539 | 4/1992 | Anderson et al. | |
| 5,194,161 | 3/1993 | Heller et al. | |
| 5,215,943 | 6/1993 | Anderson et al. | |
| 5,355,425 | * 10/1994 | Braiman et al. | 385/31 |

FOREIGN PATENT DOCUMENTS 1312227  1/1993 (CA) .

OTHER PUBLICATIONS

Hoffman, et al., "Environmental Applications of Semiconductor Photocatalysis", *Chem. Rev.* 95:69–96 (1995).

Hofstadler, et al., "New Reactor Design for Photocatalytic Wastewater Treatment with $TiO_2$ Immobilized on Fused–Silica Glass Fibers: Photomineralization of 4–Chlorophenol", *Environ. Sci. Technol.* 28:670–674 (1994).

Kamat, "Photochemistry on Nonreactive and Reactive (Semiconductor) Surfaces", *Chem. Rev.* 93(1):267–300 (1993).

Kim and Anderson, "Solution factors affecting the photocatalytic and photoelectrocatalytic degradation of formic acid using supported $TiO_2$ thin films", *J. Photochemistry and Photobiology A:Chemistry* 94:221–229 (1996).

MacCraith, "Enhanced evanescent wave sensors based on sol–gel–derived porous glass coatings", *Sensors and Actuators B* 11:29–34 (1993).

MacCraith, et al. "Sol–gel coatings for optical chemical sensors and biosensors", *Sensors and Actuators B* 29:51–57 (1995).

Marinangeli and Ollis, "Photoassisted Heterogeneous Catalysis with Optical Fibers", *AIChE Journal* 23(4):415–426 (1977).

Marinangeli and Ollis, "Photo–Assisted Heterogeneous Catalysis with Optical Fibers II. Nonisothermal Single Fiber and Fiber Bundle", *AIChE Journal* 26(6):1000–1008 (1980).

Mills et al., "Water Purification by Semiconductor Photocatalysis", *Chem. Rev.* 93:417–425 (1993).

(List continued on next page.)

Primary Examiner—Frank G. Font
Assistant Examiner—Michael P. Mooney
(74) Attorney, Agent, or Firm—Quarles & Brady LLP

(57) ABSTRACT

A waveguide comprising a transparent substrate and a metal oxide coating having the disclosed properties on the substrate can propagate light in an attenuated total reflection mode.

22 Claims, 2 Drawing Sheets

OTHER PUBLICATIONS

Peill and Hoffmann, "Mathematical Model of a Photocatalytic Fiber–Optic Cable Reactor for Heterogeneous Photocatalysis", *Environ. Sci. Technol.* 32:398–404 (1998).

Peill and Hoffmann, "Development and Optimization of a $TiO_2$–Coated Fiber–Optic Cable Reactor: Photocatalytic Degradation of 4–Chlorophenol", *Environ, Sci. Technol.* 29:2974–2981 (1995).

Sabate, et al., "A Kinetic Study of the Photocatalytic Degradation of 3–Chlorosalicylic Acid over $TiO_2$ Membranes Supported on Glass", *J. Catalysis* 127:167–177 (1991).

Serpone, Nick, "Relative photonic efficiencies and quantum yields in heterogeneous photocatalysis", *J. Photochemistry and Photobiology A: Chemistry* 104:1–12 (1997).

Xu and Anderson, "Sunthesis of porosity controlled ceramic membranes", *J. Mater. Res.,* 6(5):1073–1081 (1991).

Xu, "Physical–Chemical Factors Affecting the Synthesis and Characteristics of Transition Metal Oxide Membranes", pp. 198–233 (Thesis, Ph.D. Water Chemistry, University of Wisconsin Madison, 1991).

* cited by examiner

WAVEGUIDE

STATEMENT REGARDING FEDERALLY SPONSORED RESEARCH OR DEVELOPMENT

This invention was made with United States government support awarded by the following agencies: EPA Grant No: R822591. The United States has certain rights in this invention.

CROSS-REFERENCE TO RELATED APPLICATIONS

Not Applicable

BACKGROUND OF THE INVENTION

Optical waveguides are used in industry and science in a variety of processes and purposes and have been proposed for use in supporting and illuminating photocatalysts. Mariangeli, R. E. and D. F. Ollis, AIChE J. 23 (4): 1000 (1977). In this configuration they could be used in remediating effluent waste streams (e.g., water or air) by photocatalytic oxidation or photooxidation. Titanium dioxide ($TiO_2$) and other transition metal oxides are well-known as effective photocatalysts that can oxidize organic compounds to $CO_2$ and $H_2O$ in the presence of UV light (at wavelengths of about 380 nm or less for $TiO_2$) and a suitable electron acceptor, such as $O_2$. Metal oxide-mediated photocatalytic processes can occur at ambient temperatures. The coated waveguides can also remove inorganic ions from solution and can find utility in processes for converting ionic species into neutral species, such as metals.

Several shortcomings in metal oxide-based photocatalytic processes have been identified. For instance, (a) the ratio of illuminated catalyst surface area to reactor volume is often low, (b) the photocatalyst must be fixed in the reactor to separate from the reactant, and (c) the photocatalyst uses the activating ultraviolet radiation inefficiently. For example, UV light distribution throughout a typical $TiO_2$ packed-bed reactor design is hindered by the high UV absorptivity of $TiO_2$ and by losses due to reflection and scattering. Attempts to overcome these limitations have generally not succeeded.

For example, $TiO_2$-coated optical fibers have been used for photocatalytic oxidation of organic compounds in water. In such systems, UV light is propagated through an optical fiber substrate to photoactivate the $TiO_2$ coating. The UV light is not completely absorbed in a single coated region of the fiber. $TiO_2$-coated optical fibers as developed thus far are not an adequate solution to the identified shortcomings in that it has only been possible to propagate UV light for about 10–15 cm. Peill, N. J., and Hoffmann, M. R., "Mathematical Model of a Photocatalytic Fiber-Optic Cable Reactor for Heterogeneous Photocatalysis," *Environ. Sci. Technol.*, 32:398–404 (1998); Peill, N. J., and Hoffmann, M. R., "Development and Optimization of a $TiO_2$-Coated Fiber Optic Cable Reactor: Photocatalytic Degradation of 4-Chlorophenol," *Environ. Sci. Technol.*, 29:2974–81 (1995).

Peill and Hoffmann determined that at each reflection at the fiber/$TiO_2$ interface a portion of the UV light was refracted out of the fiber and absorbed by the $TiO_2$ coating. Successive reflections quickly diminished the UV light intensity in the fiber. According to Peill and Hoffmann, the UV light propagated through the optical fibers in a frustrated total reflection (FTR) mode which is expected when light is incident from an optically rarer medium (i.e., silica) to an optically denser medium (i.e., $TiO_2$). Peill and Hoffmann point out that "[t]he refractive index of $TiO_2$ is higher than that of fused-silica glass . . . . For this reason, it is impossible that total refection occurs at the interface . . . the light flux is divided: one part of it is reflected and the other part leaves the fiber." Peill and Hoffmann, (1998), supra.

In another approach, U.S. Pat. Nos. 5,194,161 and 4,997,576 disclose processes for oxidizing organic compounds in an oil film floating on water. These patents describe coating photocatalytic metal dioxides, including $TiO_2$, onto water-floatable waveguiding materials such as silica beads. UV light trapped in the coated bead is scattered onto the photocatalytic material where it is completely absorbed so as to create a photon flux for photocatalytic oxidation of the oil by oxygen. Although the patents envision using the coated materials to oxidize organic compounds, the patents describe preparing the coated materials so as to rapidly absorb as much trapped UV light as possible from the substrate. This approach is contrary to the articulated desire to improve the efficiency with which UV light is used in photocatalytic systems.

The art is still in need of a photocatalytic system that efficiently propagates UV light in a coated photocatalytic waveguide. Such a waveguide would allow for the controlled interaction of light energy with a large photocatalyst surface area, thus, enhancing the efficiency of heterogeneous photocatalytic processes, including but not limited to photooxidation or solar energy conversion. Such waveguides could also be the basis for novel optical chemical and biochemical sensors.

BRIEF SUMMARY OF THE INVENTION

In one aspect, the present invention is summarized in that a waveguide that propagates light in an attenuated total reflection (ATR) mode comprises a transparent internal reflection element (IRE) and a porous, particulate transition metal oxide coating on one or more surfaces of the IRE, the coating being provided so that its boundaries are parallel to the IRE surface or surfaces. The particles and pores of the coating are small relative to the wavelength of the propagating light (i.e., at most less than 1/10 size of the wavelength of the light). The pores can be mesoporous, microporous or nanoporous, depending upon the wavelength of the light to be propagated. A constant distance is maintained between the IRE/film interface and the film/external medium interface.

In another aspect, the invention is summarized in that a method for forming the waveguide of the invention includes the steps of applying a particulate metal oxide coating to a transparent IRE as described herein.

It is an object of the invention to provide an apparatus comprising a waveguide or a plurality of waveguides that propagates light in an attenuated total reflection mode and distributes the light to a photocatalytic coating on a surface of the waveguide.

Another object of the invention is to provide a photocatalyst for efficient photocatalysis.

It is a feature of the invention that a waveguide according to the invention includes a particulate coating on an IRE, where the coating has a refractive index higher than that of the transparent substrate on which the coating is coated.

It is an advantage of the invention that the waveguide propagates light in an ATR mode.

Another advantage of the metal oxide-coated waveguide of the invention is its ability to efficiently capture diffuse light (such as sunlight or light from a fluorescent lamp) for photocatalysis, for biological or chemical sensing, or for increasing the efficiency of a photovoltaic cell. Diffuse light sources are typically disfavored photoilluminators, since the intensity of light from a diffuse light source diminishes with distance from the source. Using the waveguides of the invention, especially in an apparatus comprising a plurality of waveguides, the light intensity gradient is less severe than in conventional photoreactors that are activated by direct illumination.

Yet another advantage of the present invention is that the waveguides yield the benefit of an even distribution of activated catalyst throughout the reactor volume. Furthermore, the activated photocatalyst in a waveguide reactor is evenly distributed throughout a comparatively larger reactor volume. These attributes could facilitate the economical scale-up of photocatalytic reactors to the dimensions required for commercial remediation applications. Photocatalytic reactors that incorporate the waveguides of the invention reduce the cost of UV light generation because fewer light sources are required. This particularly important for materials such as $TiO_2$ that require UV light for activation.

Other objects, advantages, and features of the present invention will become apparent after examination of the specification and claims.

DETAILED DESCRIPTION OF THE INVENTION

Figure 1:
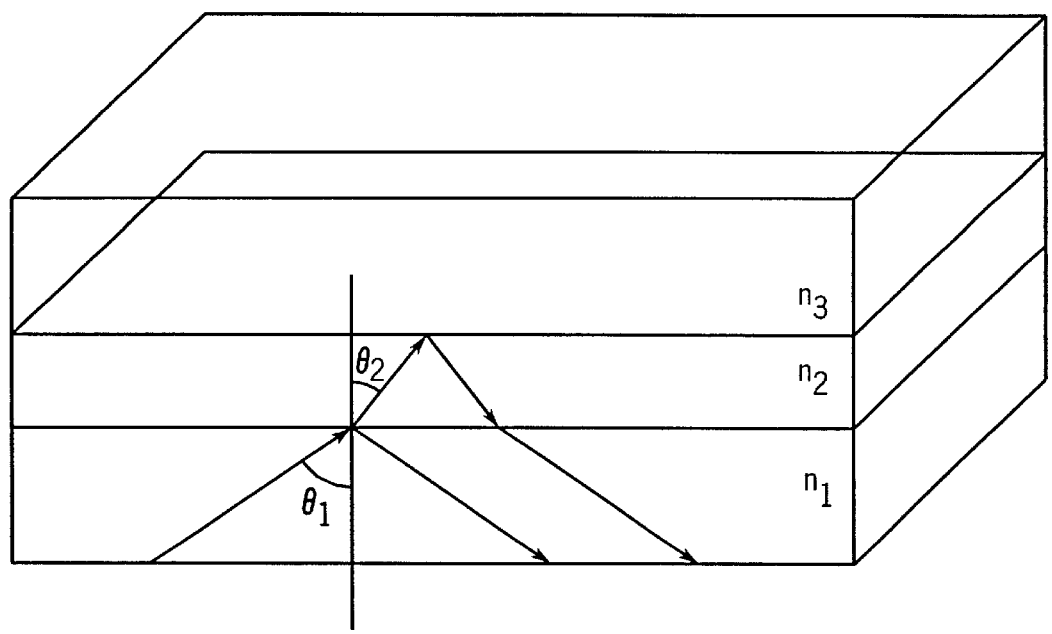
FIG. 1 depicts a schematic representation of the internal reflection of UV light at a thin-film interface.

Prior titania-coated silica waveguides propagated UV light in FTR mode, and a skilled artisan would expect FTR propagation when UV light is incident from the optically rarer medium, silica, to the optically denser medium, $TiO_2$, as was described by Peill and Hoffmann, supra. Porous $TiO_2$ has a composite refractive index of about 1.9 vs. a refractive index of 1.5 for silica.

Applicants have determined that light can be propagated through such a waveguide in an ATR mode by avoiding optical roughness in the metal oxide waveguide coating. Optical roughness is avoided by utilizing a coating selected to promote internal reflection and by applying the coating so that its boundaries (interfaces) are parallel to the substrate.

While Heller et al. (U.S. Pat. Nos. 5,194,161 and 4,997,576, supra) teach a parallel relationship between the coating and the substrate, the coating of Heller et al. is designed to be "thick enough to absorb all of the photons with energies exceeding the band-gap." (col. 22, lines 37–40) In contrast, the waveguide coating of the present invention promotes total internal reflection and propagation in an ATR mode, with only a portion of the light being absorbed at each reflection.

Photocatalytic reactors based on the waveguides of the invention may utilize light more efficiently than reactors that rely upon direct irradiance of the catalyst. By illuminating the catalyst with internally reflected light, it may be possible to increase the amount of photocatalyst illuminated in a given reactor volume and to improve the efficiency with which the incident light is employed. The waveguide can propagate light in an ATR mode without regard to whether the external environment is liquid or gaseous.

A waveguide that propagates light in an attenuated total reflection (ATR) mode comprises a transparent internal reflection element (IRE) and a particulate metal oxide coating on one or more surfaces of the IRE so that the film boundaries are parallel to the IRE surface or surfaces. The coating is preferably less than about 1 micron thick and has a more preferred thickness of between 40 and 500 nm. There is no theoretical upper limit on the thickness of the coating, although a practical limitation is about 1 micron because of scattering of the light within the $TiO_2$ film coating. The preferred thickness can vary with the intended application, although it is advantageous that the waveguide of the invention can illuminate thicker coatings than have previously been usefully coated. The coating can be a semiconductor.

The transparent IRE substrate can be a structure of any size or shape including, but not limited to, a fiber, such as an optical fiber, or planar sheet of transparent material. The element can be one of the commonly used IREs such as a glass or a plastic. For applications using UV light, a fused silica glass IRE or an acrylic IRE is preferred.

The coating comprises colloidal metal oxide particles sized and arrayed in a random close packed arrangement on the IRE substrate surface so that neither the particles nor the pores formed between particles can scatter input light of wavelengths greater than about 250 nm. This can be achieved when both the pores and the particles are no more than about $\frac{1}{10}$ of the size of the wavelength of input light. Typically, the particles and pores are much smaller than the wavelength of the propagating light (about 250 nm or greater). The particles are preferably in the range of 4 to 10 nm in diameter, and are more preferably on the order of about 5 nm. Such coatings are optically homogeneous with respect to the radiation. For visible light, a coating is optically homogenous if the coating is transparent and will not scatter light. However, if the coating appears cloudy or opaque, it will scatter light and such a waveguide will not propagate light in an ATR mode. The film coating is further characterized in that it has a porosity of about 45–55% and a pore radius of between 15 Å–40 Å. The coating also has a refractive index greater than that of the transparent substrate.

One can determine whether a photocatalyst-coated waveguide can propagate light in an ATR mode by noting whether the critical angle for total internal reflection is unchanged after deposition of the coating onto the transparent waveguide substrate. If deposition of a relatively high refractive index metal oxide coating onto a transparent substrate does not change the critical angle, such a coated substrate will propagate light in an ATR mode. The critical angle for any waveguide (measured from normal to the waveguide/film interface) can be determined in view of the disclosure that follows.

In a preferred embodiment, the metal oxide particles are titanium dioxide ($TiO_2$), silicon dioxide ($SiO_2$), manganese dioxide ($MnO_2$), a mixed titanium dioxide/zirconium dioxide ($TiO_2/ZrO_2$), or other transition metal oxides. U.S. Pat. Nos. 5,610,109; 5,439,624; 5,342,431; 5,269,926; 5,215,943; 5,104,539; 5,096,745; 5,035,784; 5,028,568; and 5,006,248, all of which are incorporated herein by reference, describe particulate metal oxides. The incorporated patents also disclose how to make metal oxide coatings from colloidal metal oxide sols. Sols made according to the method of Aguado, M. A. and M. A. Anderson, *Solar Energy Materials and Solar Cells* 28:345 (1993) (Colloid C), or by the method of Xu, Q. and M. A. Anderson, "Synthesis of porosity controlled ceramic membranes," J. Mater. Res.

6:1073–1081 (1991), both incorporated herein by reference, are also suitable, except the colloidal sol need not be concentrated after dialysis by evaporating water from the suspension.

In another preferred embodiment, a plurality of waveguides according to the invention are provided in combination so as to capture light in a photoreactor and distribute it, via an ATR mode propagation, throughout the photoreactor. The plurality of waveguides can be, but need not be, identical in size or shape to one another, but rather can be sized and shaped to maximize use of available light or fluid dynamics or another desired parameter. The light source can be external to the plurality of waveguides, or the waveguides can surround the light source in whole or in part.

The colloidal sol can be applied onto an IRE according to any method known in the art including, but not limited to, dip-coating, spin-coating, or spray coating. Through control of particle synthesis during the sol preparation process, and control of pH of the sol, it is possible to deposit multiple layers of different metal oxide films onto a variety of substrates. For example, a silica film can be deposited onto an acrylic substrate, and a $TiO_2$ film can be deposited on top of the silica. This will result in the film boundaries being parallel to each other and the acrylic substrate such that the coated structure will guide light in an ATR mode. The pH of the colloidal sol controls the particle packing, pore size, and the ability of the film to adhere to the substrate. For example, the $TiO_2$ sol described in Example 1 below adheres strongly to an $SiO_2$ substrate, and the particles will pack in such a way as to yield a porous film with boundaries parallel to the $SiO_2$ substrate.

In this system, the optical nature of the interface is determined by the refractive indices of the waveguide phases and the exterior medium (i.e., air, water, etc.). Without intending to limit the invention, applicants offer the following theory that explains the novel ability to propagate light through a waveguide in an ATR mode.

FIG. 1 shows a 3-phase system that includes two semi-infinite dielectric mediums of refractive indices $n_1$ and $n_3$ ($n_3<n_1$) separated by a dielectric medium of finite thickness with refractive index, $n_2$ ($n_2>n_1>n_3$). In preferred embodiments, described here, phase 1 is an acrylic or silica substrate, phase 2 is a mesoporous $TiO_2$ film coating as described, and phase 3 is air or water. Phases 1 and 3 are semi-infinite and transparent. Phase 2 is finite with a thickness on the order of the wavelength of the incident light. Coherent light incident from phase 1 onto phase 2 is reflected, transmitted or absorbed.

Light incident from phase 1 onto the interface is totally internally reflected (reflection=100%) if the following conditions are met:
(1) the incident angle of the light exceeds the critical angle ($\theta_c$) where $\theta_c$ is determined by $$\theta_c = \sin^{-1}(n_3/n_1) \quad (1)$$

(2) phase 2 is parallel to phases 1 and 3; and (3) phase 2 is non-absorbing and free of scattering defects.

At incident angles greater than the critical angle, the angle of refraction of phase 3 is imaginary. The presence of a film having a parallel boundary (phase 2) at the glass/air boundary does not affect the critical angle for total internal reflection. If $\theta_2$ is the critical angle for total reflection at the $TiO_2$/air interface, then $\sin \theta_2 = n_3/n_2$, and the light incident on the interface at all angles greater than $\theta_2$ will be totally reflected. From the law of refraction, $\sin \theta_2 = (n_1/n_2) \sin \theta_1$, so the critical angle for total reflection is $$\theta_c = \theta_1 = \sin^{-1}(n_3/n_2) \quad (2)$$

At incident angles greater than $\theta_c$, the reflection is total and independent of the wavelength of light and the thickness of phase 2, in the region where phase 2 is non-absorbing.

If phase 2 is absorbing, the reflection is attenuated, and a portion of the light is absorbed or scattered by phase 2 at each reflection. If the surface of phase 2 is rough relative to the wavelength of incident light, a portion of the light is transmitted into phase 3, and the reflection is said to be frustrated. While total reflection is independent of the thickness of phase 2, this thickness is practically limited to 1 micron by difficulty inherent in synthesizing a thicker optically homogeneous $TiO_2$ coating.

Accordingly, in an ATR mode, light incident upon the substrate/coating/medium interface is totally reflected back into the substrate. At each reflection, the film coating absorbs a portion of the light having greater energy than its 380 nm band gap. Given a sufficient number of reflections, the film coating will eventually absorb all of the UV light energy with no refractive losses out of the waveguide.

In operation, light, preferably ultraviolet light having a wavelength of 380 nm or less, enters the waveguide at an angle greater than the critical angle and is guided axially away from the light source via successive total internal reflections at the substrate/coating interface. The light energy is sufficient to activate the photocatalyst coating. The coating absorbs (i.e., attenuates) only a small portion of the light at each interfacial interaction. In this manner, the waveguide is said to propagate light in an ATR mode.

The extent to which the propagating UV light is attenuated depends on the loss per reflection at the film/substrate interface and the overall number of reflections per axial distance (dependent on waveguide thickness and propagation angle). For a longer waveguide in which the light must propagate farther, a thinner film is more suitable. For a shorter propagating distance (i.e., fewer reflections at the $TiO_2$/silica interface), a thicker film is preferable. Hence, it is possible to tailor waveguide geometries and sizes to meet reactor design needs by adjusting the thickness of the metal oxide film.

The disclosed photocatalyst-coated waveguides can be used in a fixed-bed reactor for, e.g., remediating polluted waste streams. The IRE both transmits light and supports the photocatalyst. This reactor configuration has several advantages over slurry-phase and conventional fixed-bed reactor designs. Direct delivery of light to the photocatalyst minimizes losses due to absorption and scattering by the reactor and reactant. The configuration also provides a more uniform distribution of the photocatalyst within the reaction solution resulting in reduced mass transport limitations to photochemical conversion and allowing for higher processing capacities. The remote transmission of light to a photocatalyst via such a system is not possible with other photocatalytic reactor configurations. As a result, the system can be utilized for in-situ remediation of contaminated subsurface contaminates or for remote, off-line treatment of either aqueous and/or vapor-phase contaminates such as chlorinated hydrocarbons.

Optical waveguide sensors for chemical and biological species based on evanescent wave (EW) interactions have also attracted considerable research interest. The disclosed invention can be used as an optical waveguide sensor. When light propagates in an optical waveguide in an ATR mode, a standing wave is established at the waveguide surface. This wave extends a short distance from the guiding region into the medium of lower refractive index which surrounds it. This evanescent field, which decays exponentially with distance from the waveguide interface, defines a short-range sensing volume within which the evanescent energy may interact with a molecular species. In the case of a waveguide coated with a porous film, the energy may interact with the film or species within the film. An associated detector can detect chemical changes at the waveguide surface.

A few distinct approaches may be adopted in these areas. First, the evanescent wave can interact directly with an analyte if the interrogating wavelength coincides with an absorption band of the species. Alternatively, an intermediate reagent, which responds optically to the analyte, may be attached to the waveguide. Often, reagent-mediated EW sensors provide a greater sensitivity than direct spectroscopic devices. Another application involves the concentration of a species by adsorption onto the porous metal oxide surface. This feature allows the propagating light to interrogate the species through absorption, scattering or fluorescence interactions. The surface of the metal oxide can also be functionalized with particular analyte-sensitive species to allow for greater specificity.

The modified waveguides of the present invention may also find use in photovoltaic cells. Because a photovoltaic cell is analogous to a photocatalytic reactor, the same efficiencies posited for photocatalytic materials may be realized by supporting and illuminating photovoltaic material.

The following examples are merely illustrative of preferred embodiments of the present invention, and are not intended, in any way, to limit the invention.

EXAMPLE 1

Preparing Colloidal Sols

Colloidal sols were prepared according to the method for making Colloid C in Aguado, M. A. and M. A. Anderson, *Solar Energy Materials and Solar Cells* 28:345 (1993), or by the method of Xu, Q. and M. A. Anderson, "Synthesis of porosity controlled ceramic membranes," J. Mater. Res. 6:1073–1081 (1991), both incorporated herein by reference, supra, except the colloidal sol was not concentrated after dialysis by evaporating water from the suspension.

Briefly, 1.43 ml of 70% $HNO_3$ was placed in a 500 ml Erlenmeyer flask containing 200 ml of laboratory grade water (18 Mohms resistance, generated by a Bamstead system) being vigorously agitated with a magnetic stir bar. To this stirred, acidified water, 16.5 ml titanium isopropoxide $(Ti(OPr^i)_4$, Aldrich Catalogue No. 20527-3) was slowly added by pouring over a glass stirring rod to form a white precipitate. The alkoxide could alternatively be added dropwise from a buret or separatory funnel. The entire mixture was continuously stirred for three (3) days to form a clear sol having a pH of about 1.5, and comprising particle aggregates of about 20 nm.

The sol was then dialyzed by placing 150 ml of the sol into a prepared length of 3500 M.W. cut-off dialysis tubing (Spectrum Medical Indus., Catalogue No. 132725). The dialysis tubing was then placed into laboratory grade water at a ratio of 10:1 (1.5 L of water for 150 ml of sol) overnight. The dialyzed water was then replaced with fresh water and the sol was once again allowed to dialyze overnight.

The water was changed, and the dialysis was repeated until the pH of the sol was between 3.0 and 3.5. The final sol is viscous (about 5.5 cP) and contains irregularly shaped particle aggregates of about 80 to 100 nm in size. The $TiO_2$ sol was approximately 2 wt. % $TiO_2$ at a pH of about 3.4. Films prepared from this sol should have a porosity of about 50% when fired, depending on the firing conditions.

Preparing $TiO_2$ Films

The $TiO_2$ sol was deposited by dip-coating at a rate of about 1 cm/min. onto one side of silica IRE's (50 mm×20 mm×2 mm parallelepipeds, Harrick Scientific Corp.). The coated IRE's were heated in a furnace (Thermolyne, Model 30400) to 350° C. at a rate of 3° C./min and were held at that temperature for two hours. Film thickness was varied from roughly 40 nm to 500 nm by repeating the coating step or by varying the speed at which the substrate was withdrawn from the sol. In general, faster withdrawal rates increased film thickness. Multiple layers yielded a homogenous uniform film.

Film thickness was determined by profilometry (Tencor Instruments, Model 200). Profilometry measurements were corroborated with SEM measurements (LEO, Model 982). Table 1 shows the relationship of the number of $TiO_2$ layers to the film thickness.

TABLE 1

$TiO_2$ film thickness

| Number of $TiO_2$ Layers | $TiO_2$ film Thickness (nm) |
|---|---|
| 1 | 35 ± 4 |
| 2 | 55 ± 5 |
| 3 | 94 ± 8 |
| 4 | 128 ± 8 |
| 5 | 150 ± 12 |

Refractive index of the $TiO_2$ films was determined by ellipsometry (Gaertner Scientific Corp. Model LI 16C) measurements made on films deposited on a silicon wafer to be 1.9±0.1. The refractive index of the film can be assumed to be a composite of the refractive index of $TiO_2$ particles and air-filled pores:

$$n_{d,film} = n_{d,air} \times X_{air} + n_{d,TiO_2} \times X_{TiO_2} \qquad (3)$$

where Xair and $XTiO_2$ are the compositional fractions of the pores and solid $TiO_2$ in the film.

Given a refractive index of 2.6 for solid, anatase $TiO_2$ the porosity of the $TiO_2$ is calculated to be 45±7%. Thus, the refractive index of the film when the pores are filled with water ($n_d$=1.33) is about 2.0. The $TiO_2$ films have a higher refractive index than the silica substrates ($n_d \approx 1.5$).

Photocatalytic Waveguide in Aqueous Environment Propagates Light in an ATR Mode

The light transmission mode of a coated photocatalytic waveguide was determined by measuring the UV-Visible internal reflection spectrum of aqueous phenolphthalein using coated and uncoated IRE's. As was noted above in the Detailed Description, uncoated IRE's transmit light in an ATR mode and one can determine whether a coated IRE retains that ability by comparing the internal reflection spectra.

UV absorbance in the region of 310–380 nm was measured using a UV-Visible spectrophotometer (Hewlett-Packard, Model HP8452) and a variable angle Internal Reflection Spectroscopy Cell Holder (Harrick Scientific Corp., Model TRMP-VAM). Transmittance and Internal Reflection Spectra of phenolphthalein (1:1 mixture of saturated phenolphthalein in methanol and 1 M NaOH in water) were obtained using the same instrument.

The internal reflection UV-Visible spectrum of phenolphthalein using both uncoated and $TiO_2$-coated silica waveguides were qualitatively similar in both cases, and resembled transmission spectra. Significant losses were only observed in the absorbing region of $TiO_2$ (<380 nm). This indicates that the light propagates through both the coated and uncoated IRE's in an ATR mode. This also demonstrated that $TiO_2$-coated silica waveguides propagate light in a water medium with no apparent refractive losses.

It was not possible to measure internal reflection spectra when the internal angle of incidence of the propagating light was less than the critical angle for the silica/water interface ($\theta_c = \sim 65° = \sin^{-1}(n_{d,\ water}/n_{d,\ silica})$). When the internal angle of incidence is below the critical angle, light propagates in FTR mode. In that case, most of the light is lost out of the crystal through refraction at the interface.

Table 2 reports the amount of incident light (at 68° angle) absorbed by the photocatalytic films of various thicknesses coated on the IRE.

TABLE 2

Percent light absorbed by $TiO_2$ film

| $TiO_2$ Film Thickness (nm) | Percent input light absorbed |
|---|---|
| 35 | 50 |
| 90 | 63 |
| 150 | 70 |
| 500 | 91 |

The percent of absorbed light was determined by comparing the transmittance through films of various thicknesses to the spectral distribution of the band-pass filter. The spectral distribution of the bandpass filter ranged from 310–380 nm with a maximum at 360 nm. The fraction of light absorbed by the various $TiO_2$ films at each wavelength was calculated as:

$$[I_0 - I/I_0]_{\lambda,\ Film} = (1 - \%T/100)_{\lambda,\ Film} \times (I_\lambda / I_{\lambda,\ max})_{filter} \quad (4)$$

The first term on the right side of equation 4 represents the fraction of light absorbed by the film at a given wavelength, and the second term is the fractional intensity of the light. The integral with respect to wavelength of the filter spectral distribution from 310 nm to 380 nm was assumed to be equal to the measured light intensity. The numerically evaluated integral over the same interval of the fractional absorbance (equation 4) was the fraction of the input intensity absorbed by the catalyst.

Since the light propagates through the coated crystal in an ATR mode, all losses are assumed to result from absorption by the $TiO_2$, or from omnidirectional scattering due to imperfections in the film. This scattering loss is observable as the decrease in percent transmittance in the non-absorbing (>380 nm) spectral region.

Waveguide in Air Propagates UV Light in an ATR Mode

As noted in the Detailed Description, it is possible to determine whether a photocatalyst-coated IRE propagates light in an ATR mode by noting whether deposition of the relatively high-refractive-index photocatalyst film changes the critical angle for total internal reflection. The critical angle was determined by measuring the relative intensity of a single reflection of 632.8 nm HeNe laser light at a silica/$TiO_2$/air interface over a range of angles bracketing the critical angle. This was accomplished by attaching to the flat face of a hemispherical prism a silica glass slide ($n_d$ = 1.515) coated with a 270 nm thick mesoporous anatase $TiO_2$ film formed of about 5 nm primary particles and characterized by a high porosity (about 50%), high surface area (>150 $m^2/g$) and a large pore radius (15 Å–40 Å). The coating had a composite refractive index of about 1.8 in air.

The laser light was shined into the prism, reflected off the silica/$TiO_2$/air interface, and measured with a photodiode detector. Transmission dropped abruptly at the predicted critical angle $(\theta_c) = \sin^{-1}(n_3(1.000)/n_2(1.515)) = 41.30°)$.

Thus, it is possible to conclude that transparent substrates coated with relatively higher refractive index metal oxide films will propagate light in an ATR mode because reflection of incident light at angles greater than the critical angle is total.

The claim of ATR propagation through silica substrates coated with porous $TiO_2$ films is further supported by observations of UV-Visible internal reflection spectra of $TiO_2$ films deposited onto silica IRE's (50 mm×20 mm×2 mm parallelepipeds, Harrick Scientific Corp.). Examinations of the spectra revealed that attenuation of internally reflected light at the silica/$TiO_2$/air interface is negligible in the visible spectrum. However, in the UV spectrum (wavelength less than 380 nm), where the $TiO_2$ is absorbing, the attenuation is marked. The attenuation increases with increasing film thickness. These observations are consistent with propagation of both visible and UV light in an ATR mode through the $TiO_2$-coated silica IRE's. Thus a silica IRE coated with porous $TiO_2$ acts as a waveguide; propagating light via successive total internal reflections at the silica/$TiO_2$/air interface.

EXAMPLE 2

Photooxidation Using $TiO_2$-Coated IRE's in Aqueous Environment

Figure 2:
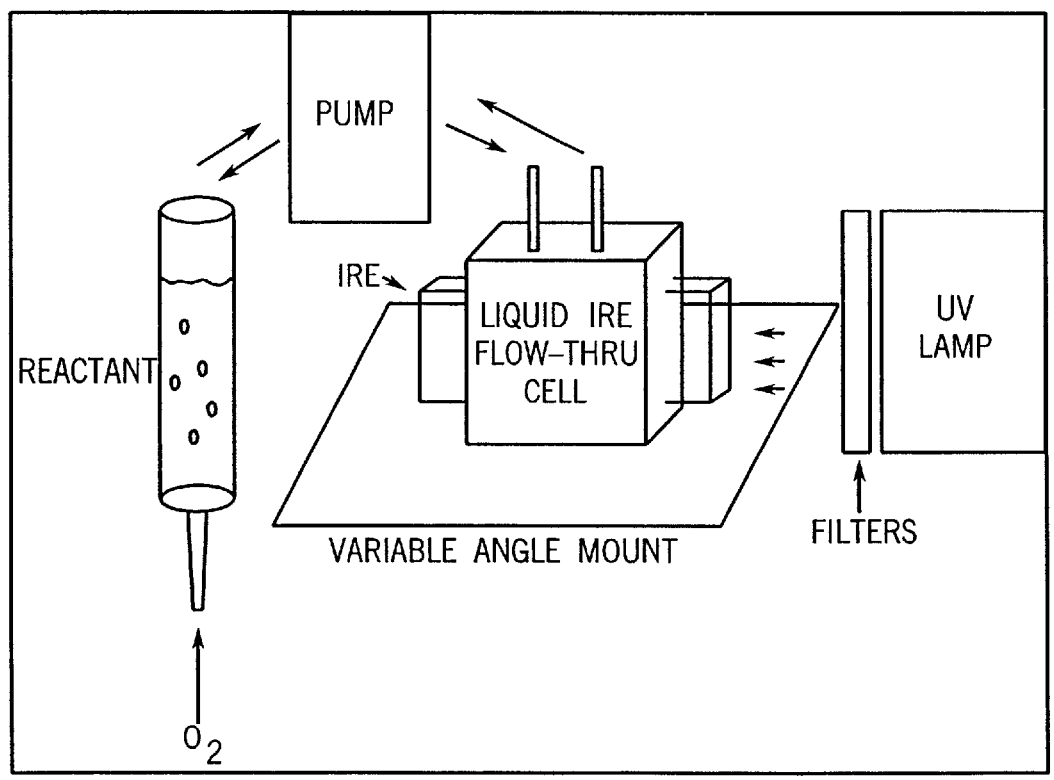
FIG. 2 is a schematic representation of a photoreactor using a $TiO_2$-coated, silica internal reflection element (IRE).

FIG. 2 depicts a continuous-flow, recirculating photooxidation reactor system. A $TiO_2$-coated silica IRE was held in a flow-through liquid cell (Harrick Scientific Corp., Model MEC-1S) mounted on a variable angle pedestal (Harrick Scientific Corp., Model TRMP-VAM) positioned in front of a UV (wavelength—310–380 nm) light source (Oriel Instruments Corp., Model 66024 lamp housing w/450 W Xe—Hg arc lamp). Light was filtered through a 10 cm IR water filter (Oriel, 6123) and a 310–380 nm UV band pass filter (Oriel, 59810). Collimated light from the source was shone on the edge of the IRE and propagated internally to the $TiO_2$ coating. Reactant solution was recirculated over the coated face of the IRE at a flow rate of 6 ml/min with a peristaltic pump (SciLog Corp., Model 1041). Oxygen was bubbled into the reaction vessel at a rate of 5 ml/min to ensure that the reactant solution was well mixed and saturated with dissolved oxygen.

Reactant concentration was monitored with a carbon analyzer (Shimadzu, Model TOC5000). Light flux to the IRE (total irradiance in $mW/cm^2$; accurate to within ±0.5 $mW/cm^2$) was measured using a radiometer (International Light Corporation). The spectral distribution was assumed to be that of the UV band pass filter (Oriel, Model 59810).

Formic acid was chosen as the target reactant because it oxidizes to $CO_2$ and $H_2O$ with no stable intermediates or byproducts. A 10 ml solution of aqueous formic acid (concentration=10 mg/L as carbon, 833 ~$\mu$mol/L) was contained in a separate vessel with a gas inlet and medium glass frit. The pH of the initial formic acid solution was 3.8. In a study by Kim, et. al, J. Photochem. Photobiol. A; Chem., 94:22 (1996), photocatalytic oxidation rates of formic acid were independent of initial concentration above 17 mg/L (4.4 mg/L as carbon, 370 $\mu$mol/L). Thus, the rate of reaction was assumed to be constant throughout the 4 hour duration of each experiment.

Rates of formic acid oxidation were based on the difference between initial formic acid concentration and the concentration remaining after 4 hours of operation. Concentration was measured as total organic carbon in the solution. A blank was run with no illumination and no decrease in formic acid concentration was detected.

$O_2$ flow rate was varied from 5 mL/min to 15 mL/min with no difference in reaction rate. Hence, the reactant was assumed to be well mixed and saturated with $O_2$.

Reactant flow rate was varied from 3 mL/min to 10 mL/min with no change in reaction rate observed.

The energy of light that propagated within the IRE was assumed to be the measured flux multiplied by the surface area of the IRE crystal edge (0.4 cm$^2$). This number was multiplied by 0.96 to account for a about 4 percent (4%) reflection loss from the crystal edge. This quantity was converted to units of $\mu$eins/hr by a factor of $1.08 \times 10^{-5}$ eins/hr per 1 mW. This conversion was based on a maximum throughput of the band-pass filter at 360 nm (i.e. E (einsteins)=Nhc/$\lambda$, $\lambda$=360 nm, 1 MW=$10^{-3}$ J/s).

It was observed that the $TiO_2$-coated waveguide effectively oxidized formic acid. In general, it was observed that thicker $TiO_2$ films oxidized formic acid faster than thinner films for a given light input. It was also observed that the photoreactor system oxidized formic acid more effectively when the light propagated through the waveguide at angles greater than the critical angle, or, in other words, when the light propagated in an ATR mode.

The waveguides of the invention have important implications for photocatalytic reactor design and for optical sensor development. Because light propagates in an ATR mode, there are no losses due to refraction. Thus, the interaction of the guided light with the porous coating can be carefully controlled through variations in overall waveguide thickness, the coating thickness and the propagation angle of the light.

The present invention is not limited to the foregoing embodiments, but encompasses all such variations and modifications as come within the scope of the appended claims.

We claim:

1. A waveguide for propagating light of a selected wavelength in an attenuated total reflection mode, the waveguide comprising;

a transparent internal reflection element (IRE); and a particulate transition metal oxide coating on one or more surfaces of the IRE, the coating having a boundary parallel to the at least one IRE surface, wherein the coating does not scatter light of the selected wavelength and has a refractive index greater than that of the IRE.

2. The waveguide of claim 1, wherein the metal oxide is selected from the group consisting of titanium dioxide ($TiO_2$), silicon dioxide ($SiO_2$), magnesium dioxide ($MnO_2$), and titanium dioxide/zirconium dioxide ($TiO_2/ZrO_2$).

3. The waveguide of claim 2, wherein the coating on the substrate is $TiO_2$.

4. The waveguide of claim 1, wherein the IRE has an elongated shape.

5. The waveguide of claim 4, wherein the IRE is selected from the group consisting of a fiber and a planar sheet.

6. The waveguide of claim 1, wherein the IRE comprises a material selected from the group consisting of a glass or a plastic.

7. The waveguide of claim 6, wherein the transparent substrate is a fused-silica glass.

8. The waveguide of claim 6, wherein the IRE comprises acrylic.

9. An apparatus for photocatalytic conversion of an organic compound; the apparatus comprising:

a waveguide coated with a photocatalyst for propagating light in an attenuated total reflection mode;

a light source for illuminating the photocatalyst with light having energy sufficient to activate the photocatalyst so that the light is propagated through the coated waveguide in an attenuated total reflection mode.

10. An apparatus as claimed in claim 9 wherein the waveguide comprises a transparent internal reflection element (IRE) and a particulate transition metal oxide coating on one or more surfaces of the IRE, the coating having a boundary parallel to the at least one IRE surface, wherein said coating has a refractive index greater than that of the IRE.

11. The apparatus of claim 10, wherein the metal oxide is selected from the group consisting of titanium dioxide ($TiO_2$), silicon dioxide ($SiO_2$), magnesium dioxide ($MnO_2$), and titanium dioxide/zirconium dioxide ($TiO_2/ZrO_2$).

12. The apparatus of claim 10, wherein the coating on the substrate is $TiO_2$.

13. The apparatus of claim 10, wherein the IRE has an elongated shape.

14. The apparatus of claim 13, wherein the IRE is selected from the group consisting of a fiber and a planar sheet.

15. The apparatus of claim 10, wherein the IRE comprises a material selected from the group consisting of a glass or a plastic.

16. The apparatus of claim 15, wherein the transparent substrate is a fused-silica glass.

17. The apparatus of claim 15, wherein the IRE comprises acrylic.

18. A method for making a waveguide, the method comprising the step of:

applying to an internal reflection element (IRE) a parallel coating of a particulate metal oxide coating having an index of refraction greater than that of the IRE.

19. A method as claimed in claim 18, wherein the IRE is selected from the group consisting of a fiber and a planar sheet.

20. A method as claimed in claim 18, wherein the IRE comprises a material selected from the group consisting of a glass or a plastic.

21. A method as claimed in claim 20, wherein the transparent substrate is a fused-silica glass.

22. A method as claimed in claim 20, wherein the IRE comprises acrylic.

* * * * *